(12) United States Patent
Penna

(10) Patent No.: US 9,351,724 B2
(45) Date of Patent: May 31, 2016

(54) CIRCULAR STAPLING INSTRUMENT

(71) Applicant: Covidien LP, Mansfield, MA (US)

(72) Inventor: Christopher Penna, Guilford, CT (US)

(73) Assignee: Covidien LP, Mansfield, VA (US)

( * ) Notice: Subject to any disclaimer, the term of this patent is extended or adjusted under 35 U.S.C. 154(b) by 647 days.

(21) Appl. No.: 13/739,246

(22) Filed: Jan. 11, 2013

(65) Prior Publication Data

US 2014/0197225 A1 Jul. 17, 2014

(51) Int. Cl.
*A61B 17/068* (2006.01)
*A61B 17/115* (2006.01)
*A61B 17/072* (2006.01)

(52) U.S. Cl.
CPC ........... *A61B 17/068* (2013.01); *A61B 17/1155* (2013.01); *A61B 17/072* (2013.01); *A61B 2017/07214* (2013.01)

(58) Field of Classification Search
CPC ............. A61B 17/068; A61B 17/0686; A61B 17/072; A61B 17/07207; A61B 17/115; A61B 17/1155; A61B 2017/07214
USPC ........................... 227/19, 175.2, 176.1, 180.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |

(Continued)

FOREIGN PATENT DOCUMENTS

| | | |
|---|---|---|
| CA | 908529 | 8/1972 |
| DE | 1057729 B | 5/1959 |

(Continued)

*Primary Examiner* — Scott A. Smith

(57) ABSTRACT

A circular stapling instrument including a stapling forming assembly that is actuated independently from actuation of the cutting assembly is provided. The instrument includes a handle assembly, an elongate body extending from the handle assembly, a cartridge assembly mounted on a distal end of the elongate body. The cartridge assembly includes a pusher assembly and a knife assembly. The knife assembly is selectively fixed relative to the pusher assembly.

19 Claims, 10 Drawing Sheets

(56) References Cited

U.S. PATENT DOCUMENTS

| | | |
|---|---|---|
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Bianco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,432 A * | 5/1997 | Schulze ........... A61B 17/07207 227/176.1 |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |

(56) References Cited

U.S. PATENT DOCUMENTS

| | | |
|---|---|---|
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,805,273 B2 * | 10/2004 | Bilotti ............... A61B 17/1114 227/176.1 |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,134,587 B2 * | 11/2006 | Schwemberger .... A61B 17/072 227/175.1 |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,207,472 B2 * | 4/2007 | Wukusick ........... A61B 17/072 227/176.1 |
| 7,210,609 B2 * | 5/2007 | Leiboff ............... A61B 17/115 227/180.1 |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |

(56) References Cited

U.S. PATENT DOCUMENTS

| | | |
|---|---|---|
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky et al. |
| 8,453,906 B2 * | 6/2013 | Huang ............ A61B 17/07207 227/175.2 |
| 9,010,605 B2 * | 4/2015 | Olson ................ A61B 17/1155 227/175.1 |
| 9,038,882 B2 * | 5/2015 | Racenet ............... A61B 17/072 227/176.1 |
| 2003/0111507 A1 | 6/2003 | Nunez |
| 2005/0051597 A1 | 3/2005 | Tolendano |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2005/0187576 A1 * | 8/2005 | Whitman ............ A61B 17/115 606/219 |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0112327 A1 * | 4/2009 | Lane ....................... A61B 19/20 623/17.19 |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1 | 3/2010 | Milliman et al. |
| 2010/0065607 A1 | 3/2010 | Orban, III et al. |
| 2010/0084453 A1 | 4/2010 | Hu |
| 2010/0089971 A1 | 4/2010 | Milliman et al. |
| 2010/0108739 A1 | 5/2010 | Holsten et al. |
| 2010/0108740 A1 | 5/2010 | Pastorelli et al. |
| 2010/0108741 A1 | 5/2010 | Hessler et al. |
| 2010/0133319 A1 | 6/2010 | Milliman et al. |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | WO 8706448 A | 11/1987 |
| WO | WO 8900406 A1 | 1/1989 |
| WO | WO 9006085 A1 | 6/1990 |
| WO | WO 01/54594 A1 | 8/2001 |
| WO | WO 2008/107918 A1 | 9/2008 |

* cited by examiner

CIRCULAR STAPLING INSTRUMENT

BACKGROUND

1. Technical Field

The present disclosure relates to circular stapling instruments. More particularly, the present disclosure relates to a circular stapling instrument having independent strokes for forming staples and cutting tissue.

2. Background of Related Art

Circular staplers are known, as are their use in closed procedures, i.e., endoscopic, laparoscopic or through natural body orifices. Typically the circular staplers include a tool assembly on a distal end of an elongate body. The tool assembly includes a mechanism for forming staples and a knife for cutting the stapled tissue. Actuation of the tool assembly may be performed by a manually operated trigger or a powered drive assembly. Generally, both the actuation of the staple forming mechanism and the advancement of the knife occur at the same time, i.e., simultaneously. Thus, the force provided by the actuation assembly must be sufficient to overcome the force required to form the staples and the force required to advance the knife through the tissue being stapled. Further, the simultaneous actuation of the staple forming mechanism and advancement of the knife requires that the staple forming mechanism and the knife travel the same distance, thereby limiting the staple formation height to the knife travel distance.

Therefore, it would be beneficial to have a circular stapler including a tool assembly configured to form staples independently of cutting tissue.

SUMMARY

Accordingly, a circular stapler including a stapling forming assembly that is actuated independently from actuation of the cutting assembly is provided. The circular stapler including, a handle assembly, an elongate body extending from the handle assembly, and a cartridge assembly mounted on a distal end of the elongate body. The cartridge assembly includes a pusher assembly and a knife assembly. The knife assembly is selectively fixed relative to the pusher assembly for independent movement relative to the pusher assembly. The knife assembly is initially detached from the pusher assembly in a first stroke and subsequently attached to the pusher assembly in a second stroke.

In one embodiment, the pusher assembly includes a pusher adapter configured to be advanced a first distance and retracted a second distance, the second distance being greater than the first distance. The knife assembly may support a snap ring therearound and the pusher adapter includes a ridge formed about an inner surface thereof configured to engage the snap ring of the knife assembly.

In some embodiments, the knife assembly includes a knife carrier, a knife supported on and extending distally from the knife carrier and a snap ring supported around a proximal portion of knife carrier. The knife carrier may include an annular groove configured to accommodate the snap ring when the snap ring is in a radially compressed condition and when the snap ring is in an uncompressed condition. The snap ring may not extend beyond an outer diameter of the knife carrier when the snap ring is in the compressed condition. The snap ring may extend beyond an outer diameter of the knife carrier when the snap ring is in the uncompressed condition. The knife carrier may further include a step formed in the annular groove configured to engage the snap ring when the snap ring is in the uncompressed condition. The step may be configured to prevent radial compression of the snap ring during a tissue cutting stroke. The cartridge assembly may include a housing having an outer cylindrical portion and an inner cylindrical portion, wherein the pusher assembly and knife assembly are substantially cylindrical and are selectively received between the inner and outer cylindrical portions of the housing.

Also provided is a method of stapling tissue, including the steps of providing a surgical stapling instrument having a pusher and a knife assembly, wherein the knife assembly is selectively connected relative to the pusher assembly for independent movement relative to the pusher assembly, advancing the pusher assembly to cause an ejection and a forming of staples, retracting a pusher adapter of the pusher assembly, and advancing the pusher adapter to cause an advancement of the knife assembly and a cutting of tissue. The method may further include the step of providing a lapse of time between the ejection and forming of the staples and the cutting of tissue to allow for tissue normalization. The step of retracting the pusher adapter may include retracting the pusher adapter to a location proximal of an initial location of the pusher adapter.

DESCRIPTION OF THE DRAWINGS

Embodiments of a surgical stapling instrument including a cartridge assembly that is actuated independently from actuation of the cutting assembly are disclosed herein with reference to the drawings, wherein.

DETAILED DESCRIPTION

An embodiment of the presently disclosed circular stapling instrument including independently actuated staple forming and tissue cutting operations will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
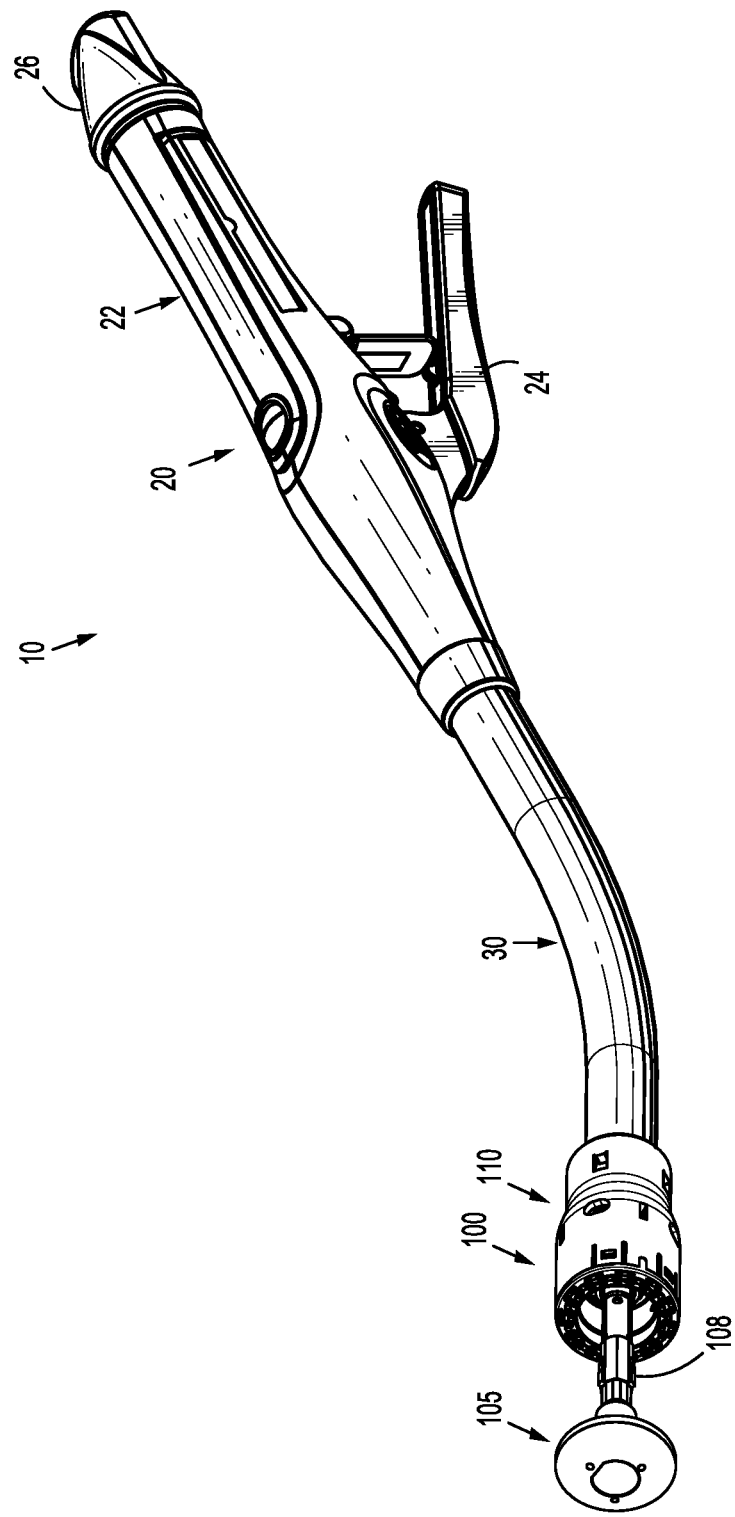
FIG. 1 is a perspective view of a surgical stapling instrument including a cartridge assembly according to an embodiment of the present disclosure.

FIG. 1 illustrates an embodiment of a circular stapling instrument according to the present disclosure, shown generally as circular stapler 10. Circular stapler 10 includes a handle assembly 20 and an elongate body 30 extending distally from handle assembly 20. A tool assembly 100 is mounted on a distal end of elongate body 30. Handle assembly 20 includes a fixed handle 22 and a moveable handle or trigger 24. Handle assembly 20 also includes an adjustment knob 26 for moving an anvil assembly 105 relative to cartridge assembly 110 of tool assembly 100. The structure and function of handle assembly 20 will only be described herein to the extent necessary to fully disclose the operation of tool assembly 100. It is envisioned that tool assembly 100 may be modified for use with any actuation assembly, powered or manual, capable of two independent actuation strokes. Commonly owned U.S. patent application Ser. No. 12/946,082, filed Nov. 15, 2010, the content of which is incorporated by reference herein in its entirety, discloses a surgical device having a powered actuator assembly including first and second drive members. In addition, it is envisioned that the independent actuation strokes may be completed by the same drive member completing two strokes or by two separate drive members.

Figure 2:
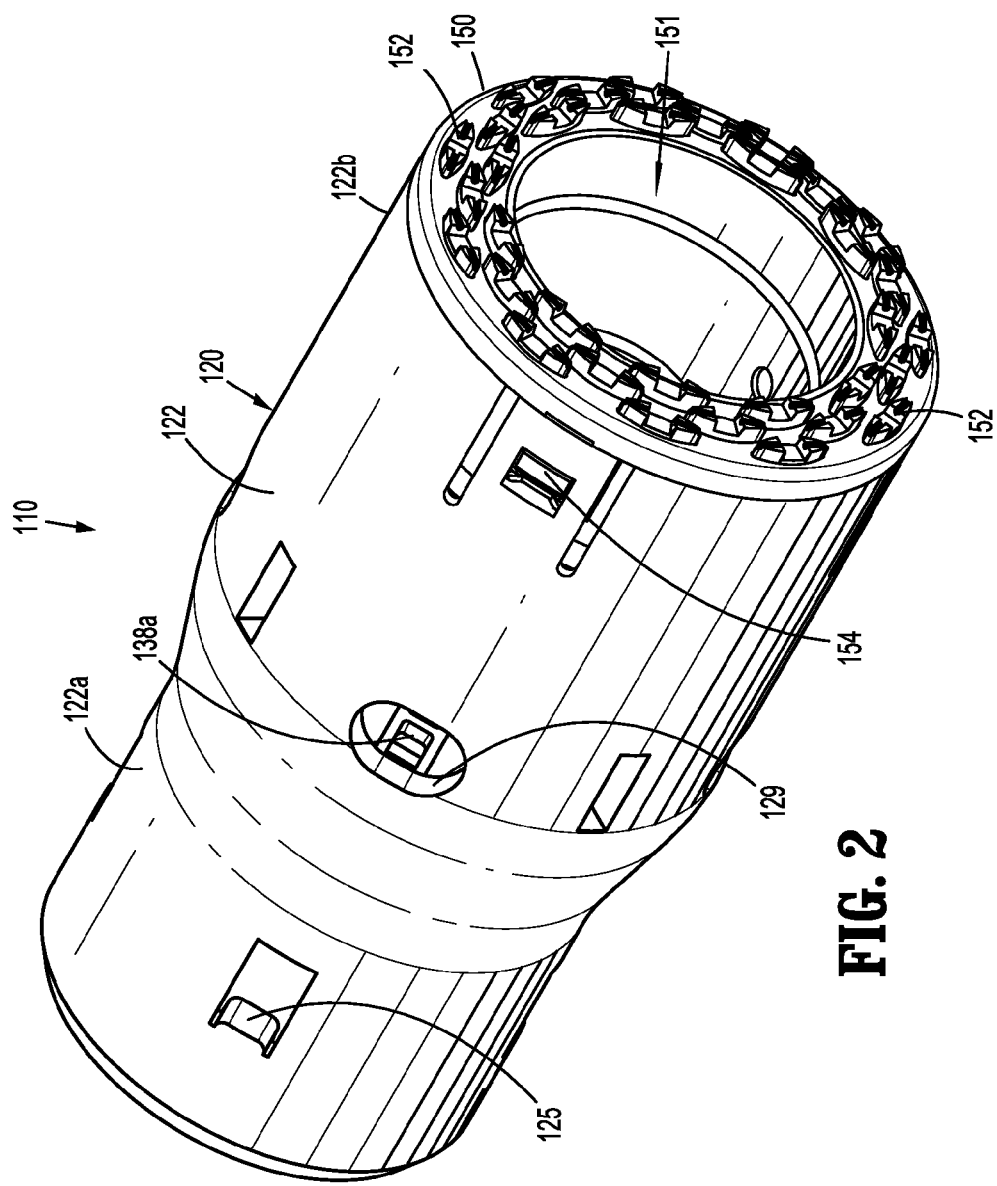
FIG. 2 is an enlarged perspective view of the cartridge assembly of the surgical stapling instrument of FIG. 1.

With reference to FIG. 2, cartridge assembly 110 of tool assembly 100 is operably mounted to a distal end of elongate body 30 (FIG. 1) of circular stapler 10 (FIG. 1). In one embodiment, cartridge assembly 110 is removably secured to elongate body 30 such that cartridge assembly 110, or a portion thereof, may be replaced and circular stapler 10 may be reused. In another embodiment, only a portion of cartridge assembly 110 is configured to be removed, and subsequently replaced or reloaded. Alternatively, circular stapler 10 may be configured for a single use, i.e., disposable.

Figure 3:
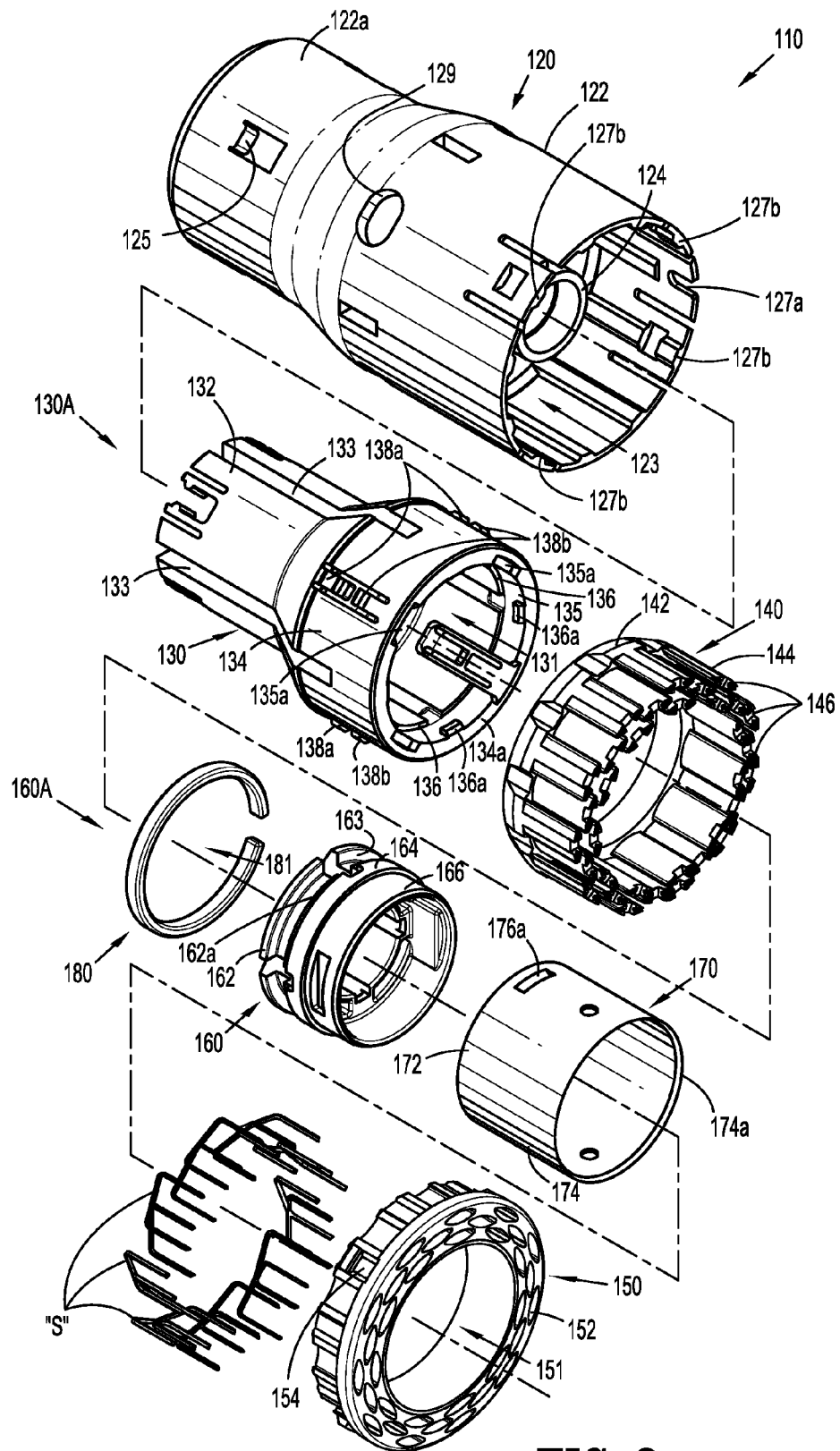
FIG. 3 is an exploded perspective view of the cartridge assembly of FIG. 2.
Figure 4:
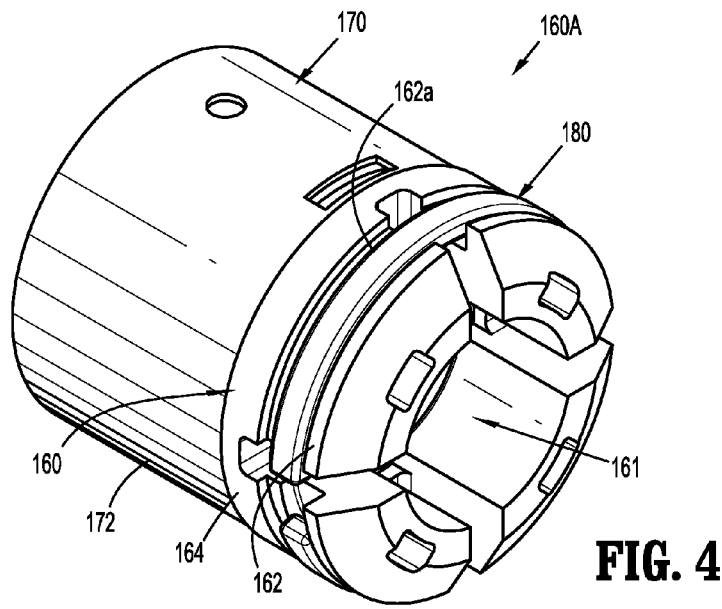
FIG. 4 is a perspective view of a knife assembly of the cartridge assembly of FIG. 2.

With reference to FIGS. 2 and 3, cartridge assembly 110 includes a housing 120, a pusher assembly 130A, a staple cartridge 150, and a knife assembly 160A. Housing 120 of cartridge assembly 110 includes an outer cylindrical portion 122, an inner cylindrical body 124 and a plurality of radially extending supports or ribs (not shown) extending between and interconnecting inner cylindrical portion 124 and outer cylindrical portion 122. Inner cylindrical portion 124 and outer cylindrical portion 122 are coaxial and define a recess 123 therebetween configured to receive a distal portion of pusher assembly 130A and knife assembly 160A.

With continued reference to FIGS. 2 and 3, a proximal end 122a of outer cylindrical portion 122 of housing 120 includes a plurality of tabs 125 formed thereon configured to operably engage cartridge assembly 110 with a distal end of elongate body 30 (FIG. 1). Distal end 122b of outer cylindrical portion 122 of housing 120 forms a plurality of tabs 127b formed therein configured to be received within notches 154 formed in staple cartridge 150. Distal end 122b of outer cylindrical portion 122 of housing 120 also defines a slot 127a configured to receive a projection (not shown) formed on staple cartridge 150. Slot 127a is positioned such that when the projection is received in slot 127a, tabs 127b formed on outer cylindrical portion 122 of housing 120 are properly aligned with notches 154 formed in staple cartridge 150. Outer cylindrical portion 122 of housing 120 further defines a plurality of openings 129. As will be discussed in further detail below, each of the plurality of openings 129 is configured to engage a pair of a plurality of detents 138a, 138b formed on a distal portion 134 of pusher adapter 130.

With reference now to FIG. 3, pusher assembly 130A includes a pusher adapter 130 and a pusher 140. Pusher adapter 130 is a substantially cylindrical member having a proximal portion 132 and a distal portion 134. Proximal portion 132 of pusher adapter 130 is configured for operable engagement with a drive member (not shown). Distal portion 134 of pusher adapter 130 is configured to operably engage pusher 140. As will be discussed in further detail below, pusher 140 is not securely affixed to pusher adapter 130 such that pusher 140 remains in an advanced position during the retraction of pusher adapter 130 following the first or stapling stroke of circular stapler 10. In this manner, the force required to move pusher adapter 130 during the second or tissue cutting stroke of circular stapler 10 does not include the force necessary to move pusher 140.

With continued reference to FIG. 3, pusher adapter 130 defines a longitudinal passage 131 extending therethrough. A distal end of longitudinal passage 131 is sized and configured to receive knife assembly 160A in a sliding manner. Pusher adapter 130 further defines a plurality of longitudinal slots 133 extending along a length thereof. Slots 133 correspond in size and location to the supports (not shown) formed between and interconnecting outer and inner cylindrical portions 122, 124 in housing 120. Pusher adapter 130 is configured to be received within outer cylindrical portion 122 of housing 120 and about inner cylindrical portion 124 of housing 120. In this manner, slots 133 receive the respective supports (not shown) of housing 120 such that inner cylindrical portion 124 of housing 120 may be received within longitudinal passage 131 of pusher adapter 130. Pusher adapter 130 defines a notch 135 on a distal end thereof which creates a distal facing ledge 136 extending about an inner surface thereof. As will be discussed in further detail below, notch 135 is configured to receive an outer annular portion of a snap ring 180 of knife assembly 160A and a ledge 136 is configured to engage the outer annular portion of snap ring 180 during the second or cutting stroke of circular stapler 10. A plurality of recesses 135a are formed in a distal surface 134a of pusher adapter 130 and are configured to engage tabs (not shown) formed on a proximal facing surface of pusher 140. A plurality of radially inwardly extending tabs 136a is spaced distal of ledge 136. As will be discussed in further detail below, tabs 136a are configured to retain snap ring 180 in engagement within a distal end of pusher adapter 130. As discussed above, pusher adapter 130 includes a plurality of paired detents 138a, 138b configured to be selectively received within openings 129 formed in outer cylindrical portion 122 of housing 120.

With reference still to FIG. 3, pusher 140 includes a proximal portion 142 and a distal portion 144. Proximal portion 142 of pusher 140 defines a plurality of tabs (not shown) configured to be selectively received within the plurality of recesses 135a formed on distal surface 134a of pusher adapter 130.

As will also be discussed in further detail below, at the completion of the second or cutting stroke of circular stapler 10 pusher assembly 130A is completely retracted relative to housing 120. In the completely retracted position, pusher 140 is disengaged from pusher adapter 130. In this manner, pusher 140 and staple cartridge 150 may be separated from housing 120.

With continued reference to FIG. 3, distal portion 144 of pusher 140 includes a plurality of pusher members 146 extending distally therefrom and arranged in three concentric rows. Pusher members 146 align with staples "S" received within staple cartridge 150 such that advancement of pusher 140 relative to staple cartridge 150 causes ejection of staples "S" from staple cartridge 150.

With reference to FIGS. 2 and 3, staple cartridge 150 is a substantially cylindrical member configured to operably engage distal end 122b of outer cylindrical portion 122 of housing 120 and defines a longitudinal opening 151 configured to receive knife 170 of knife assembly 160A therethrough. Staple cartridge 150 includes a plurality of staple receiving pockets 152 disposed about opening 151 arranged in three concentric rows. Staple receiving pockets 152 align with pusher members 146 formed on distal portion 144 of pusher 140. As discussed above, staple cartridge 150 also includes a plurality of notches 154 and a protrusion (not shown). Notches 154 are configured to operably engage distal portion 122b of outer cylindrical portion 122 of housing 120 and the protrusion (not shown) of staple cartridge 150 is configured to be received in slot 127a of outer cylindrical portion 122 to assure the proper alignment of staple cartridge 150 with outer cylindrical portion 122 of housing 120.

Figure 5:
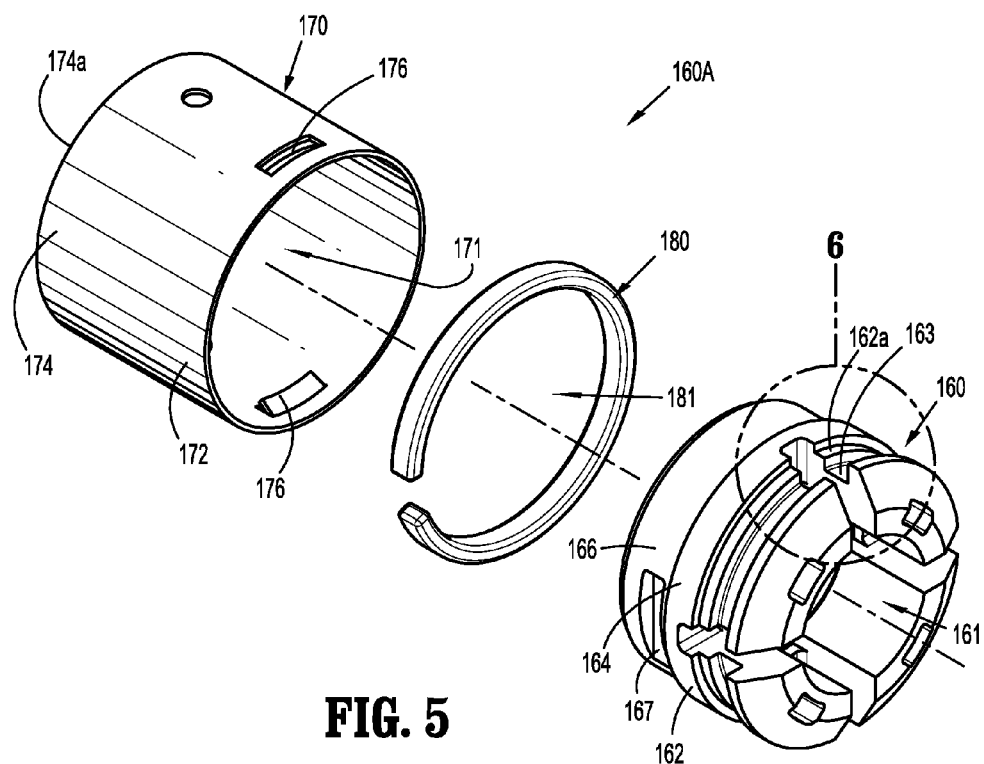
FIG. 5 is an exploded view of the knife assembly of FIG. 4.

With reference now to FIGS. 3-7, knife assembly 160A includes a knife carrier 160, a circular knife 170, and a snap ring 180. With particular reference to FIG. 5, knife carrier 160 is a substantially cylindrical member having a proximal portion 162, a distal portion 166 and an annular ridge 164 formed therebetween. Knife carrier 160 is configured to be longitudinally translatable through longitudinal passageway 131 of pusher adapter 130. Knife carrier 160 defines a longitudinal passage 161 extending therethrough. Proximal portion 162 of knife carrier 160 defines an annular groove 163 configured to accommodate snap ring 180 when snap ring 180 is in either a first or compressed condition or in a second or expanded condition. As will be discussed in further detail below, when circular stapler 10 is in the first or initial position, and prior to retraction of pusher adapter 130 following the first stroke of circular stapler 10, snap ring 180 is received completely within annular groove 163 formed in knife carrier 160. Proximal portion 162 of knife carrier 160 further defines a step 162a formed in annular groove 163. As will be discussed in further detail below, step 162a is configured to engage an inner annular portion of snap ring 180 when snap ring 180 is in the second or expanded condition. As will also be discussed in further detail below, engagement of snap ring 180 with step 162a prevents radial compression of snap ring 180 during the second or tissue cutting stroke.

Figure 6:
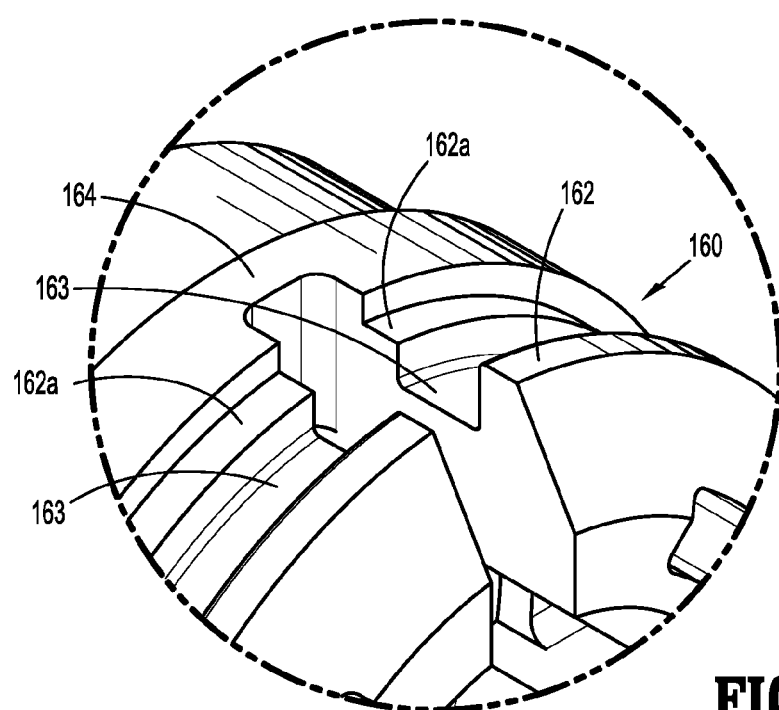
FIG. 6 is an enlarged view of the indicated portion of FIG. 5.

With continued reference to FIGS. 5 and 6, annular ridge 164 extends radially outward from between proximal and distal portions 162, 166 of knife carrier 160. Annular ridge 164 is configured to engage a proximal end of snap ring 180. Distal portion 166 of knife carrier 160 is configured to receive snap ring 180 and circular knife 170 thereabout. In particular, as seen in FIGS. 3 and 5, distal portion 166 defines a pair of opposed recesses 167 configured to engage respective locking tabs 176 formed on knife 170.

With particular reference still to FIG. 5, knife 170 is a substantially cylindrical member having proximal and distal ends 172, 174 and defining a longitudinal opening 171 extending therethrough. Knife 170 is sized and configured to be received through longitudinal opening 141 of staple cartridge 140. Distal end 174 of knife 170 includes a sharpened surface 174a defining a knife edge configured for cutting tissue. As discussed above, proximal end 172 of knife 170 is configured to be received about distal portion 166 of knife carrier 160 and includes a pair of opposed tabs 176 configured to be received within respective recesses 167 formed in distal portion 166 of knife carrier 160.

Figure 7:
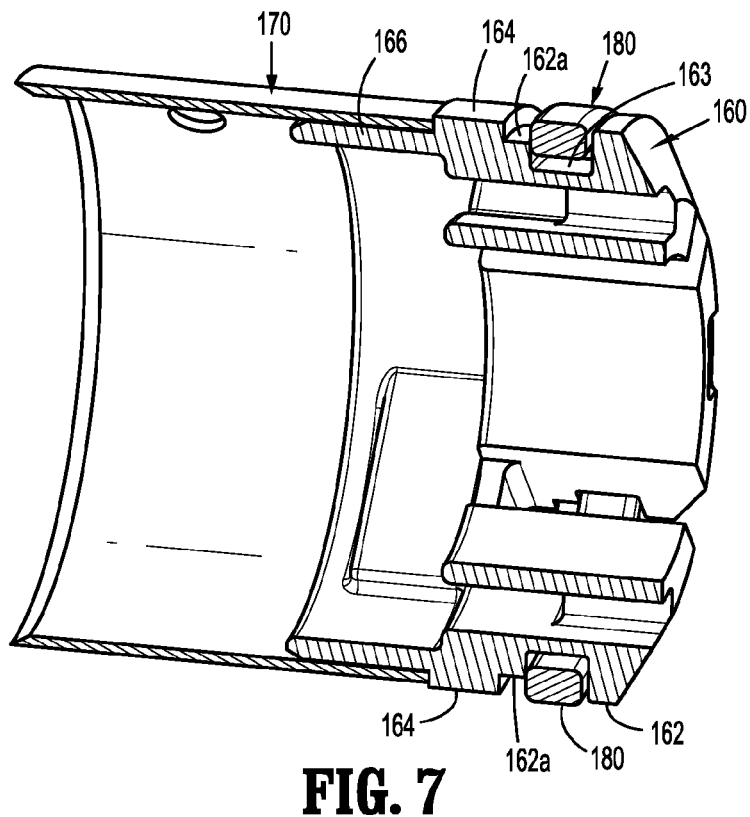
FIG. 7 is a cross-section side view of the knife assembly of FIG. 4.
Figure 10:
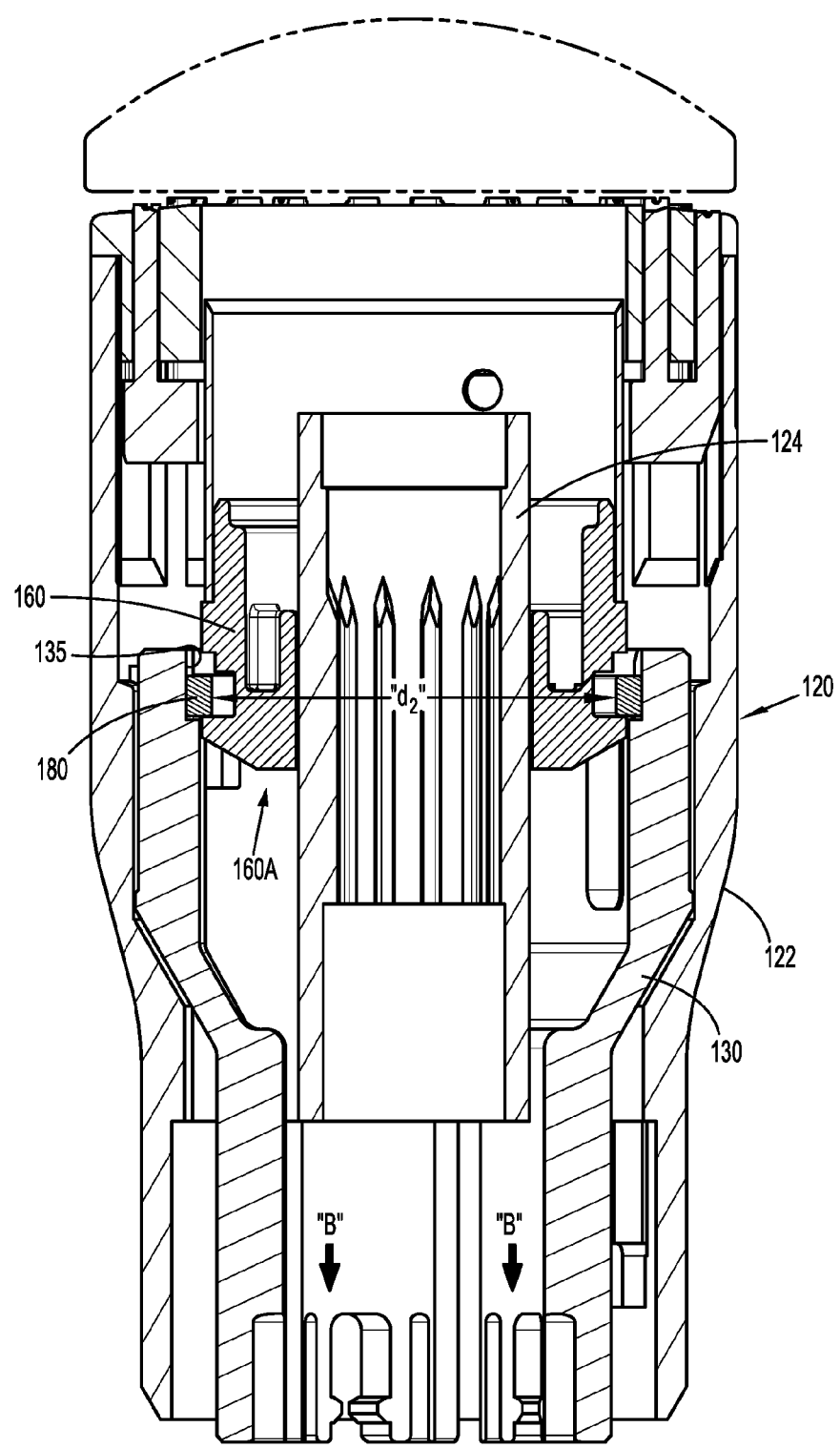
FIG. 10 is a cross-sectional side view of the cartridge assembly of FIG. 2, in a retracted position following the first or staple forming stroke.

With reference to FIGS. 5-7, snap ring 180 is a substantially C-shaped member having a substantially rectangular transverse cross-sectional profile and defining a central passage 181 therethrough. Snap ring 180 includes a first diameter "$d_1$" when in the first or radially compressed condition (FIG. 8) and a second diameter "$d_2$" when in the second or uncompressed condition (FIG. 10).

When in the first or radially compressed condition, snap ring 180 is sized to be substantially entirely received within annular groove 163 formed in proximal portion 162 of knife carrier 160. As such, when in the radially compressed condition, no portion of snap ring 180 extends beyond an outer diameter of knife carrier 160, thereby permitting relative movement between pusher adapter 130 and knife carrier 160.

When in the second or uncompressed condition, snap ring 180 is sized to simultaneously engage pusher adapter 130 and knife carrier 160. In particular, an outer annular portion of snap ring 180 is configured to engage ledge 136 created in the distal end of pusher adapter 130 by notch 135 and an inner annular portion of snap ring 180 is configured to engage knife carrier 160 adjacent step 162a formed therein. As noted above, and as will be discussed in further detail below, step 162a formed in knife carrier 160 prevents radial compression of snap ring 180 during the second or tissue stapling stroke of circular stapler 10.

Figure 8:
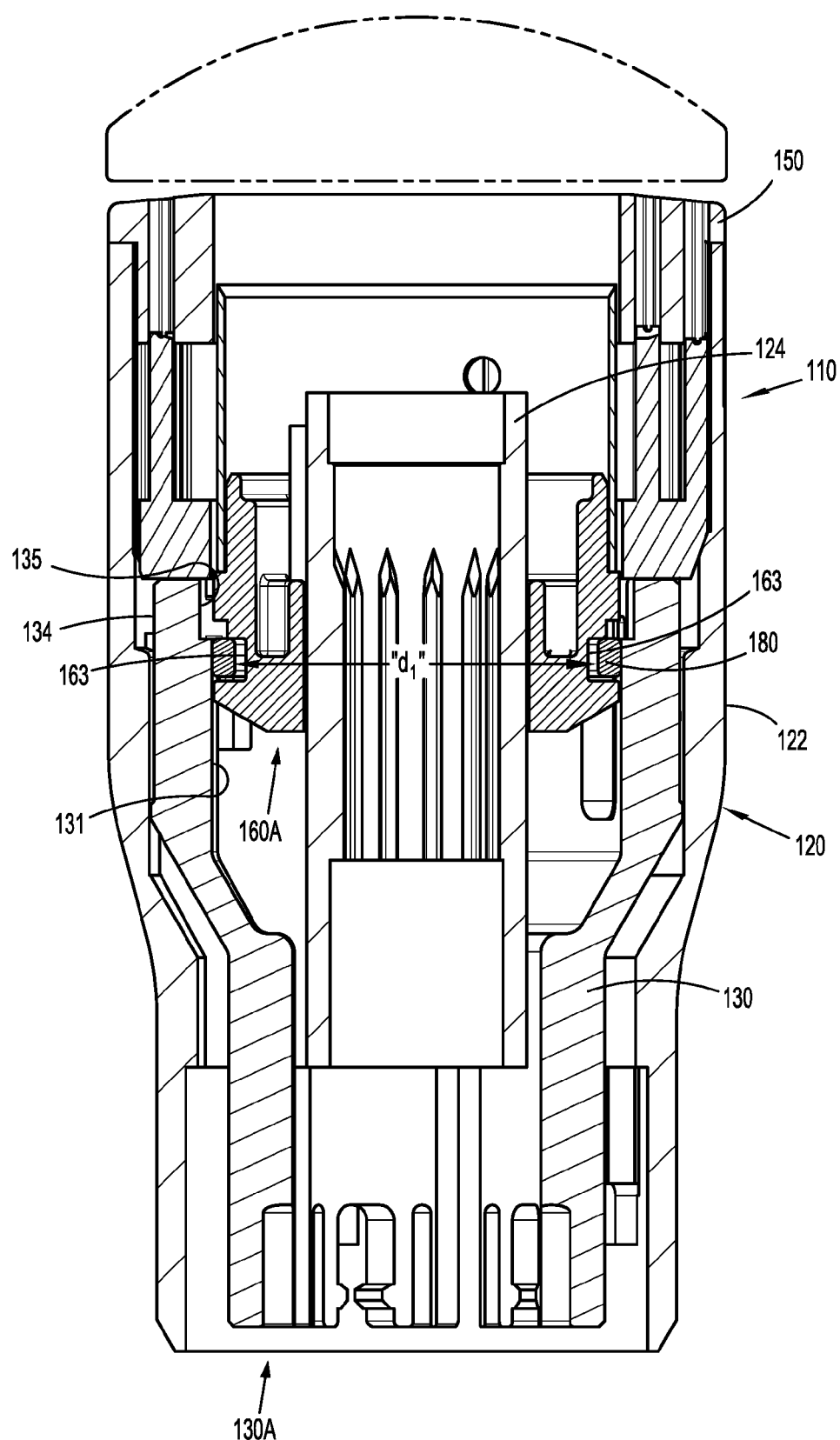
FIG. 8 is a cross-sectional side view of the cartridge assembly of FIG. 2, in a first or initial position.

The operation of cartridge assembly 110 will now be described with reference to FIGS. 8-12. Referring initially to FIG. 8, cartridge assembly 110 is shown in a first or initial condition. In the initial condition, pusher assembly 130A is received between outer and inner cylindrical portions 122, 124 of housing 120. Knife assembly 160A is received within longitudinal passage 131 of pusher adapter 130 and about inner cylindrical portion 124 of housing 120. Staple cartridge 150 is in operative engagement with distal end 120b of housing 120 to operably retain pusher assembly 130A and knife assembly 160A within housing 120. Snap ring 180 is in the first or radially compressed condition and received within annular groove 163 formed on knife carrier 160. Snap ring 180 is maintained in the radially compressed condition by an inner wall of pusher adapter 130. Notch 135 formed in the distal end of pusher adapter 130 is disposed distal of annular groove 163 and snap ring 180. In this manner, pusher assembly 130A may be advanced distally without causing the advancement of knife assembly 160A.

In the initial position, pusher assembly 130A is prevented from inadvertent distal advancement relative to housing 120 through engagement of the plurality of paired detents 138a, 138b (FIG. 3) formed on distal portion 134 of pusher adapter 130 with openings 129 (FIG. 2) formed in outer cylindrical portion 122 of housing 120.

Figure 9:
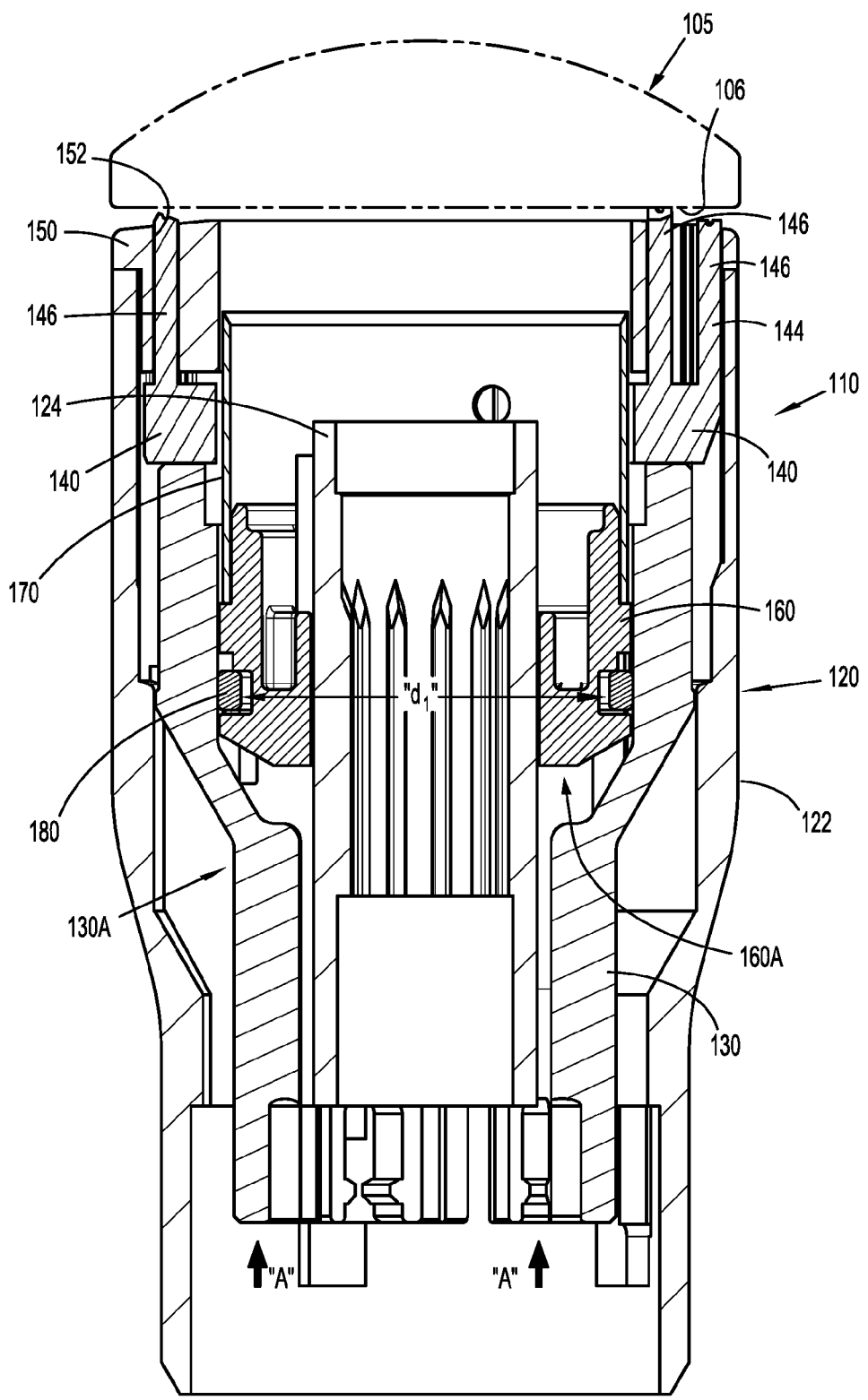
FIG. 9 is a cross-sectional side view of the cartridge assembly of FIG. 2, after the completion of the first or staple forming stroke.

With reference now to FIG. 9, during a first or staple forming stroke of circular stapler 10 (FIG. 1), following approximation of anvil assembly 105 against cartridge assembly 110, retraction or actuation of trigger 24 (FIG. 1) relative to handle 22 (FIG. 1) causes advancement of a drive assembly (not shown) which operably engages pusher adapter 130 to cause the advancement of pusher assembly 130A, as indicated by arrows "A". Advancement of pusher adapter 130 advances pusher 140 thereby causing pusher members 146 on distal portion 144 thereof to be advanced into and/or through staple receiving pockets 152 of staple cartridge 150 and to eject staples "S" from staple cartridge 150. Although not show, the ejection of staples "S" (FIG. 3) from staple cartridge 150 causes advancement of staples "S" against an anvil 106 of anvil assembly 105. Anvil 106 defines a plurality of recesses or forming pockets (not shown) corresponding in number and location to pockets 152, and being shaped to form staples "S". Forming of staples "S" secures the tissue retained between staple cartridge 150 and anvil assembly 105.

During the stapling stroke, knife assembly 160A may be maintained or held in place relative to housing 120 through engagement of one or more protrusions (not shown) formed on an inner surface of knife carrier 160 and/or on an outer surface of inner cylindrical portion 124 of housing 120 with one or more corresponding detents (not shown) formed on the other of the outer surface of inner cylindrical portion 124 and the inner surface of knife carrier 160.

With reference to FIG. 10, upon completion of the stapling stroke, pusher adapter 130 is retracted proximally relative to housing 120, as indicated by arrows "B", to a position proximal of its initial position (FIG. 8) prior to the staple forming stroke. Pusher 130 is sufficiently retracted relative to knife carrier 160 and snap ring 180 such that snap ring 180 is aligned with notch 135 formed in the distal end of pusher adapter 130. Alignment of notch 135 with snap ring 180 allows snap ring 180 to move from the first or compressed condition (FIG. 8) to the uncompressed condition, i.e., snap ring 180 is able to decompress or radially expand.

Figure 11:
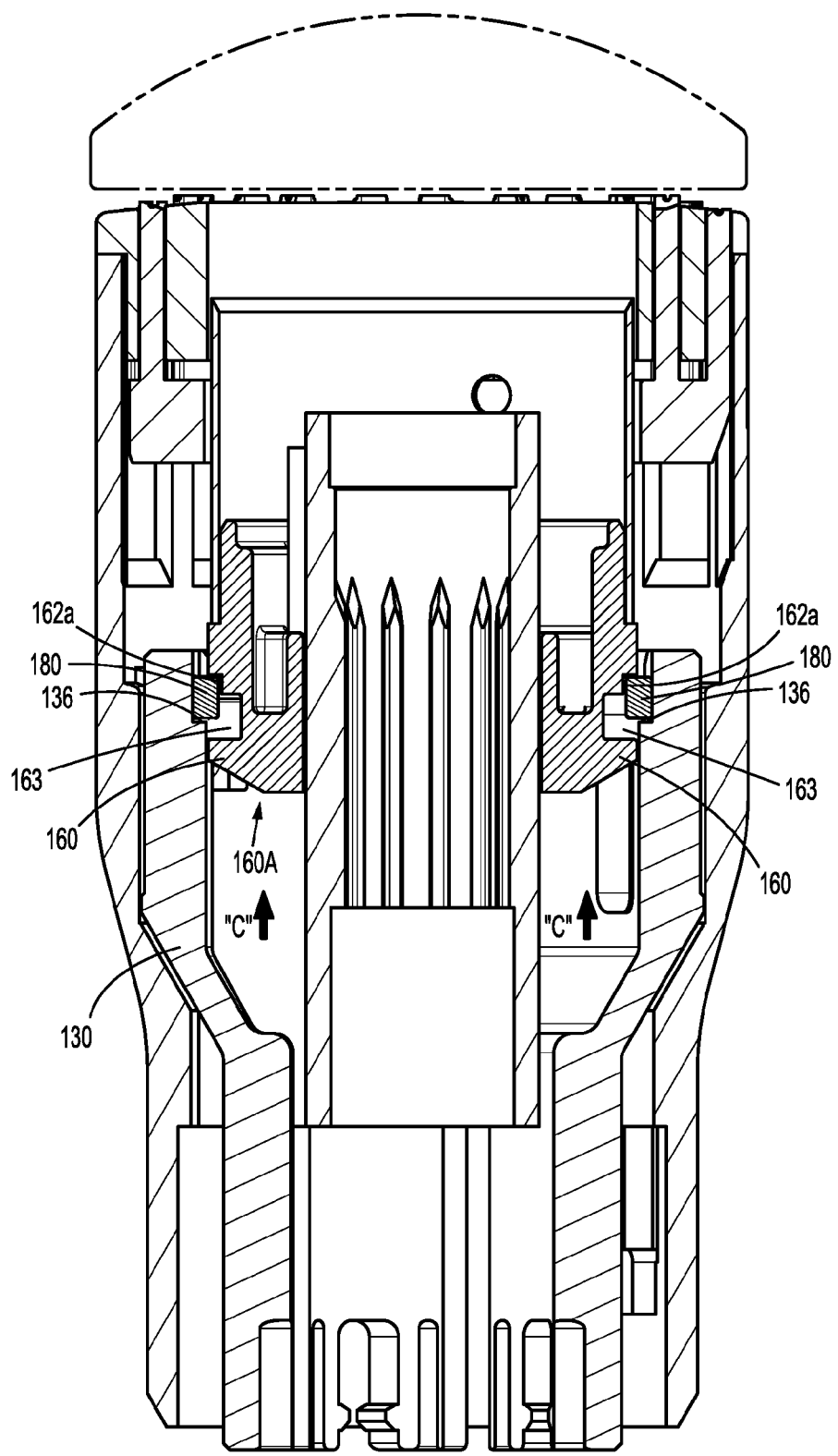
FIG. 11 is a cross-sectional side view of the cartridge assembly of FIG. 2, during a second or tissue cutting stroke.

With reference now to FIG. 11, during the second or cutting stroke of circular stapler 10 (FIG. 1), a second retraction or actuation of trigger 24 (FIG. 1) relative to handle 26 (FIG. 1) causes advancement of the drive member (not shown) which operably engages pusher adapter 130 to cause the advancement of pusher adapter 130, as indicated by arrows "C". Advancement of pusher adapter 130 causes ledge 136, defined by notch 135 formed in the distal end of pusher adapter 130, to engage an outer portion of snap ring 180 while an inner portion of snap ring 180 remains engaged with knife carrier 160. In particular, step 162a, formed within groove 163 of knife carrier 160, engages snap ring 180 and prevents snap ring 180 from being radially compressed back into annular groove 163 during the second advancement of pusher adapter 130 during the second or tissue cutting stroke of circular stapler 10. Accordingly, step 162a of knife carrier 160 maintains snap ring 180 in the second or expanded condition such that snap ring 180 remains in contact with both pusher adapter 130 and knife carrier 160 to assure the simultaneous advancement of knife assembly 160A with the advancement of pusher adapter 130, as indicated by arrows "C".

Figure 12:
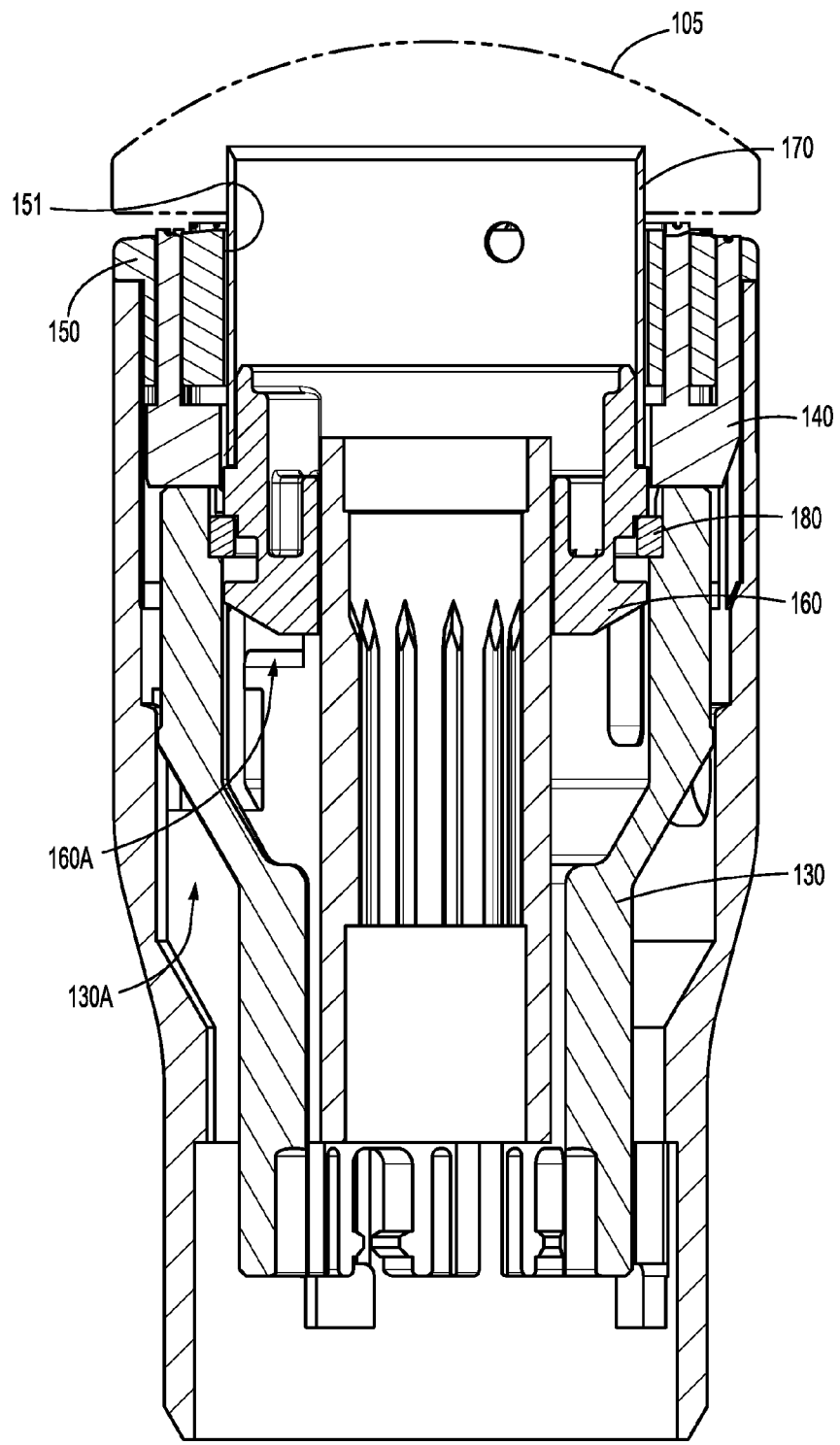
FIG. 12 is a cross-sectional side view of the cartridge assembly of FIG. 2, after the completion of the second or tissue cutting stroke.

Turning to FIG. 12, continued advancement of pusher adapter 130 causes knife 170 to be received through longitudinal opening 151 of staple cartridge 150, thereby severing the tissue retained between staple cartridge 150 and anvil assembly 105. It is envisioned that pusher assembly 130A and knife assembly 160A may be configured such that retraction of the drive assembly (not shown) causes the retraction of pusher adapter 130 and pusher 140 of pusher assembly 130A, and knife carrier 160, knife 170 and snap ring 180 of knife assembly 160A.

The use of circular stapler 10 will now be described with reference to the figures, namely FIGS. 1 and 8-12. In use, circular stapler 10 is operated in a manner substantially similar to a traditional circular stapler. Once oriented such that the tissue to be stapled is received between cartridge assembly 110 and anvil assembly 105 and anvil assembly 105 is approximated towards cartridge assembly 110, trigger 24 may be squeezed to cause the actuation of handle assembly 20. As discussed above, actuation of handle assembly 20 causes a first advancement of a drive assembly (not shown) which engages and causes the advancement of pusher assembly 130A. During the first or staple forming stroke, pusher assembly 130A is moved relative to housing 120 and knife assembly 160A while knife assembly 160A remains stationary relative to housing 120. In this manner, during the first or staple forming stroke of circular stapler 10 only the staple forming function is performed. Accordingly, the force required for completion of the first stroke of circular stapler 10 does not include the force necessary to also cut the tissue simultaneously therewith.

Upon completion of the first or staple forming stroke, trigger 24 (FIG. 1) is released to permit the retraction of the drive member (not shown) and pusher adapter 130 of pusher assembly 130A. As discussed above, pusher adapter 130 is retracted to a position proximal of its initial position. In one embodiment, pusher adapter 130 is retracted 0.25 inches further back from its initial starting position. In this retracted position, notch 135 formed in the distal end of pusher adapter 130 is aligned with snap ring 180 thereby allowing snap ring 180 to expand from the first or compressed condition (FIG. 8) to the second or uncompressed condition (FIG. 10).

A subsequent squeezing or actuation of trigger 24 causes a second advancement of the drive member and pusher adapter 130. Advancement of pusher adapter 130 causes engagement of ledge 136 of pusher adapter 130 with snap ring 180. Since snap ring 180 remains engaged with knife carrier 160 in addition to engagement with pusher adapter 130, advancement of pusher adapter 130 causes the advancement of knife assembly 160A. Advancement of circular knife 170 of knife assembly 160A causes the cutting of tissue positioned between cartridge assembly 110 and anvil assembly 105. Because staples "S" were ejected and formed during the first stroke of circular stapler 10, and pusher 140 remained in the advanced position (FIG. 9) upon retraction of pusher adapter 130 following the first or staple forming stroke, the force required to complete the second or cutting stroke of circular stapler 10 is less then the force that would be necessary to complete both the staple ejecting/forming and tissue cutting procedure. It is envisioned that the force provided by the drive member during the second stroke would be sufficient to disengage any securing mechanism maintaining knife assembly 160A relative to inner cylindrical housing 124 of housing 120. As discussed above, the securing mechanism may include protrusions (not shown) formed on the inner surface of knife carrier 160 and/or on the outer surface of inner cylindrical portion 124 of housing 120 configured to be received within detents (not shown) formed on the other of the outer surface of inner cylindrical portion 124 and/or on the inner surface of knife carrier 160 such that knife assembly 160A is permitted to advance distally relative to housing 120.

Upon completion of the tissue cutting stroke, pusher adapter 130 is retracted proximally to one of the initial position (FIG. 8) or the retracted position (FIG. 11). As discussed above, pusher assembly 130A and knife assembly 160A may be configured such that either or both of pusher assembly 130A and knife assembly 160A are retracted following the second or cutting stroke of circular stapler 10 (FIG. 1). Refraction of pusher adapter 130 to one of the initial or retracted positions causes disengagement of pusher 140 from pusher adapter 130. In this manner, pusher 140 and empty staple cartridge 150 may be separated or unloaded from housing 120 and replaced with a new pusher 140 and staple cartridge 150.

In addition to the reduced force requirements provided by the two stroke operation of circular stapler 10, the independent or decoupled staple forming and tissue cutting function of circular stapler 10 also permits the varying of the staple crimp height relative to the knife travel distance, the varying of the staple travel speed relative to the knife travel speed, and/or the addition of a dwell time between staple formation and tissue cutting. This configuration allows a clinician to optimize staple crimp heights to given conditions, such as, tissue thickness, tissue compliance and clamping force. This configuration may also allow for the monitoring of staple forming and knife cutting forces, to alert the clinician in case an abnormal force is detected. This configuration further allows force and other data to be monitored and used for data collection and research, which when analyzed, may lead to further optimization of operational parameters, such as staple crimp height and dwell and travel speed. By independently controlling and optimizing these various parameters, improved hemostasis and anastomonic joint strength may result across a much broader range of tissue thicknesses, thereby allowing a clinician to have improved and customized control over the results. Further still, when the stapling and cutting functions are performed at the same time, the tissue being stapled may be displaced by the knife, thereby causing the staple legs to deflect and misalign with their intended anvil pockets, resulting in poor staple formation and possible leakage.

It will be understood that various modifications may be made to the embodiment disclosed herein. For example, circular stapler 10 may include a mechanism for changing cartridge assembly 110 from two stroke operation to a single stroke operation. Therefore, the above description should not be construed as limiting, but merely as exemplifications of particular embodiments. Those skilled in the art will envision other modifications within the scope and spirit of the claims appended hereto.

The invention claimed is:

1. A circular stapler comprising:
a handle assembly;
an elongate body extending from the handle assembly; and,
a cartridge assembly mounted on a distal end of the elongate body, the cartridge assembly including a pusher assembly, a knife assembly received within the pusher assembly, and a compression member disposed between the pusher assembly and the knife assembly and movable between a compressed condition and an expanded condition, wherein the knife assembly is selectively fixed relative to the pusher assembly by the compression member for independent movement of the pusher assembly relative to the knife assembly, the knife assembly being initially detached from the pusher assembly during a first stroke of the handle assembly when the compression member is in the compressed condition, and subsequently attached to the pusher assembly during a second stroke of the handle assembly when the compression member is in the expanded condition, wherein the knife pusher is configured to maintain the compression member in the expanded condition during the second stroke.

2. The circular stapler of claim 1, wherein the pusher assembly includes a pusher adapter configured to be advanced a first distance and retracted a second distance, the second distance being greater than the first distance.

3. The circular stapler of claim 2, wherein the compression member includes a snap ring, the knife assembly supporting the snap ring therearound, the pusher adapter includes a ridge formed about an inner surface thereof configured to engage the snap ring.

4. The circular stapler of claim 3, wherein the knife assembly includes a knife carrier, and a knife supported on and extending distally from the knife carrier.

5. The circular stapler of claim 4, wherein the knife carrier includes an annular groove configured to accommodate the snap ring when the snap ring is in a radially compressed condition and when the snap ring is in an uncompressed condition.

6. The circular stapler of claim 5, wherein the snap ring extends beyond an outer diameter of the knife carrier when the snap ring is in the uncompressed condition.

7. The circular stapler of claim 5, wherein the knife carrier further includes a step formed in the annular groove configured to engage the snap ring when the snap ring is in the uncompressed condition.

8. The circular stapler of claim 7, wherein the step is configured to prevent radial compression of the snap ring during a tissue cutting stroke.

9. The circular stapler of claim 4, wherein the snap ring is maintained within an outer diameter of the knife carrier when the snap ring is in the compressed condition.

10. The circular stapler of claim 1, wherein the cartridge assembly includes a housing having an outer cylindrical portion and an inner cylindrical portion, wherein the pusher assembly and knife assembly are substantially cylindrical and are selectively received between the inner and outer cylindrical portions of the housing.

11. A cartridge assembly for a circular stapler, the cartridge assembly comprising:
a shell;
a pusher assembly movably disposed within the shell;
a knife assembly received within the pusher assembly; and
a compression member supported between the pusher assembly and the knife assembly, the compression member being movable between a compressed condition in which the pusher the pusher assembly and the knife assembly are independently movable to an expanded condition in which the pusher assembly and the knife assembly are connected by the compression member and movable in unison, wherein the knife assembly is configured to prevent the compression member from moving from the expanded condition back to the compressed condition.

12. The circular stapler of claim 11, wherein the compression member includes a snap ring, the knife assembly supporting the snap ring therearound, the pusher adapter includes a ridge formed about an inner surface thereof configured to engage the snap ring.

13. The circular stapler of claim 12, wherein the knife assembly includes a knife carrier, and a knife supported on and extending distally from the knife carrier.

14. The circular stapler of claim 13, wherein the knife carrier includes an annular groove configured to accommodate the snap ring when the snap ring is in a radially compressed condition and when the snap ring is in an uncompressed condition.

15. The circular stapler of claim 14, wherein the snap ring is maintained within an outer diameter of the knife carrier when the snap ring is in the compressed condition.

16. The circular stapler of claim 15, wherein the snap ring extends beyond an outer diameter of the knife carrier when the snap ring is in the uncompressed condition.

17. The circular stapler of claim 16, wherein the knife carrier further includes a step formed in the annular groove configured to engage the snap ring when the snap ring is in the uncompressed condition.

18. The circular stapler of claim 17, wherein the step is configured to prevent radial compression of the snap ring during a tissue cutting stroke.

19. The circular stapler of claim 11, wherein the cartridge assembly includes a housing having an outer cylindrical portion and an inner cylindrical portion, wherein the pusher assembly and knife assembly are substantially cylindrical and are selectively received between the inner and outer cylindrical portions of the housing.

\* \* \* \* \*